US006829379B1

(12) United States Patent
Knoplioch et al.

(10) Patent No.: US 6,829,379 B1
(45) Date of Patent: Dec. 7, 2004

(54) METHODS AND APPARATUS TO ASSIST AND FACILITATE VESSEL ANALYSIS

(75) Inventors: Jerome Knoplioch, Neuilly sur Seine (FR); Gilles R. Moris, Boulogne-Billancourt (FR); Fabienne Betting, Paris (FR); Bob L. Beckett, Wales, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 602 days.

(21) Appl. No.: 09/723,084

(22) Filed: Nov. 27, 2000

(51) Int. Cl.[7] ................................................. G06K 9/00
(52) U.S. Cl. ....................................................... 382/131
(58) Field of Search ............................... 382/128, 130, 382/131, 132; 378/4, 21, 22, 23, 24, 25, 26, 27, 63, 165; 250/363.04, 370.09, 583; 600/425, 427

(56) References Cited

U.S. PATENT DOCUMENTS

| | | | |
|---|---|---|---|
| 4,920,573 A | 4/1990 | Rhodes et al. | 382/131 |
| 5,285,786 A | 2/1994 | Fujii | 600/425 |
| 5,357,550 A | 10/1994 | Asahina et al. | 378/98.5 |
| 5,458,126 A | 10/1995 | Cline et al. | 600/425 |
| 5,699,799 A | 12/1997 | Xu et al. | 600/407 |
| 5,771,308 A * | 6/1998 | Florent | 382/130 |
| 5,782,762 A * | 7/1998 | Vining | 600/407 |
| 5,891,030 A * | 4/1999 | Johnson et al. | 600/407 |
| 6,047,080 A | 4/2000 | Chen et al. | 382/128 |
| 6,148,095 A * | 11/2000 | Prause et al. | 382/131 |
| 6,169,917 B1 | 1/2001 | Masotti et al. | 600/407 |
| 6,195,445 B1 * | 2/2001 | Dubuisson-Jolly et al. | 382/107 |
| 6,272,366 B1 * | 8/2001 | Vining | 600/407 |
| 6,301,498 B1 | 10/2001 | Greenberg et al. | 600/427 |
| 6,501,848 B1 * | 12/2002 | Carroll et al. | 382/128 |

FOREIGN PATENT DOCUMENTS

| | | | |
|---|---|---|---|
| FR | 2 623 642 | 5/1989 | G06F/15/72 |
| WO | WO 97/48978 | 12/1997 | G01N/23/04 |
| WO | WO 01/37219 | 5/2001 | G06T/11/00 |
| WO | WO 01/80185 | 10/2001 | G06T/11/00 |

OTHER PUBLICATIONS

International Search Report, dated Nov. 26, 2002, application No. PCT/US 01/47082, 7 pages.
Rubin, Geoffrey D., et al., "Perspective Volume Rendering of CT and MR Images: Applications for Endoscopic Imaging," Radiology, vol. 199, No. 2, May 1, 1996, pp. 321–330, XP-002083446.

* cited by examiner

Primary Examiner—Andrew W. Johns
Assistant Examiner—Shervin Nakhjavan
(74) Attorney, Agent, or Firm—Carl B. Horton, Esq.; Armstrong Teasdale LLP

(57) ABSTRACT

One embodiment of the present invention is a method for analyzing tubular structures in a patient, including steps of: selecting a region of interest and a location within the region of interest from a displayed tube-shaped tree representative of a tubular structure in a patient; identifying a centerline of a structure within the tube-shaped tree within the region of interest; and displaying one or more views of the region of interest. The view or views are selected from at least a segmented 3-D view having the region of interest identified, a curved view of the selected branch, a reformatted view dependent upon the identified centerline, and a 3-D view dependent upon the identified centerline.

28 Claims, 11 Drawing Sheets

METHODS AND APPARATUS TO ASSIST AND FACILITATE VESSEL ANALYSIS

BACKGROUND OF THE INVENTION

This invention relates generally to methods and apparatus for analysis of vessel images, and more particularly to methods and apparatus for assisting medical care personnel such as radiologists in preparing measurements and reports for surgical planning from images derived from computed tomographic, MR, and 3D radiation imaging.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

One of the important applications of computed tomographic (CT) imaging, as well as magnetic resonance (MR) imaging and 3-D x-ray imaging, is vascular analysis. X-ray quantification and analysis of vessel pathologies are important for radiologists who are called upon to assess stenosis or aneurysm parameters, quantify lengths, section sizes, angles, and related parameters. It would be desirable for these measurements to be performed in a consistent and repeatable manner so that referring physicians can rely upon them for surgical planning. Radiologists are also expected to provide thorough visual reports. For productivity reasons, as well as to reduce film costs, these visual reports need to be limited to only a small set of significant images.

3D visualization software provides a set of tools to perform length, angle or volume measurements and to visualize a volume in different ways, for example, using cross-sections, navigator or volume rendering. Known methods for quantification and analysis of vessel pathologies require an extensive array of tools to localize possible lesions, and then to perform measurements. Such methods are highly operator dependent, and require both time and software expertise. For example, a trained operator may need more than one hour to complete a single abdominal aorta aneurysm case. Even with trained operators given all the required time, results are not particularly reproducible and there are no consistent reporting frameworks. Furthermore, some measurements, such as true 3D-length measurement along vessels, cannot be performed using known manual tools. Because of these limitations, only a small number of sites are able to provide high-quality reports.

It would therefore be desirable to provide methods and apparatus assisting in the analysis of vessels and other structures that would assist operators in rapidly providing high-quality, consistent reports.

BRIEF SUMMARY OF THE INVENTION

There is therefore provided, in one embodiment of the present invention, a method for analyzing tubular structures in a patient, including steps of: selecting a region of interest and a location within the region of interest from a displayed tube-shaped tree representative of a tubular structure in a patient; identifying a centerline of a structure within the tube-shaped tree within the region of interest; and displaying one or more views of the region of interest. The view or views are selected from at least a segmented 3-D view having the region of interest identified, a curved view of the selected branch, a reformatted view dependent upon the identified centerline, and a 3-D view dependent upon the identified centerline.

Embodiments of the present invention, including the embodiment described above, provide quick, easy, consistent, and full reports, without requiring excessive training or software expertise.

BRIEF DESCRIPTION OF THE DRAWINGS

The negative images in FIGS. 9, 10, 11, and 12 correspond to the images in FIGS. 3, 4, 5, and 8, with reference numerals omitted.

DETAILED DESCRIPTION OF THE INVENTION

Figure 1:
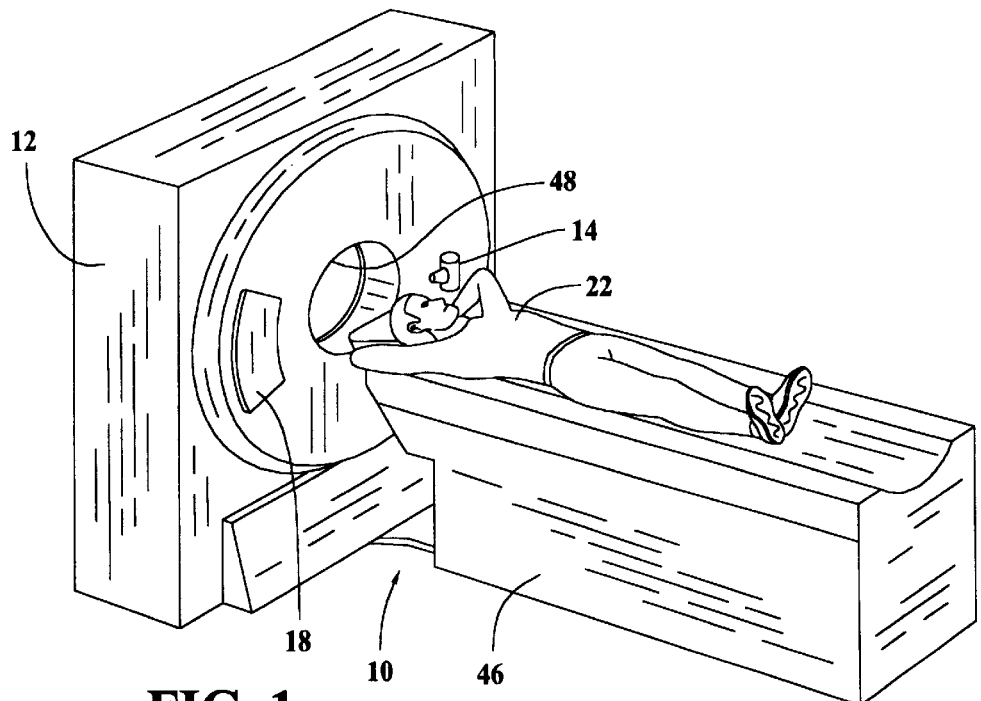
FIG. 1 is a pictorial view of a CT imaging system.
Figure 2:
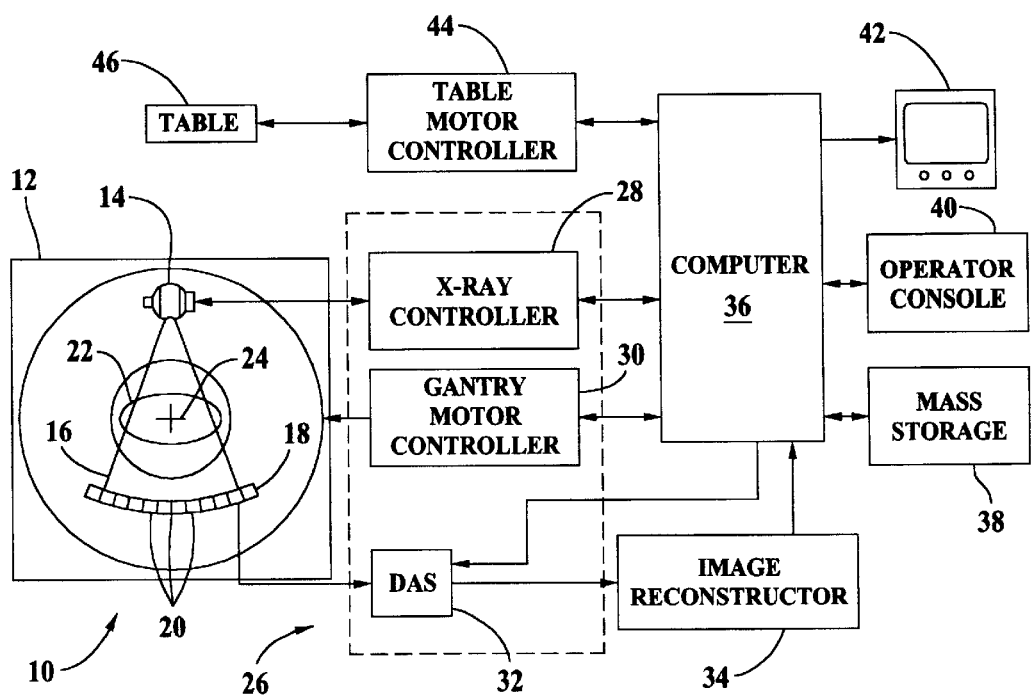
FIG. 2 is a block schematic diagram of the system illustrated in FIG. 1.

In one embodiment of the present invention, computed tomographic images are used. Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
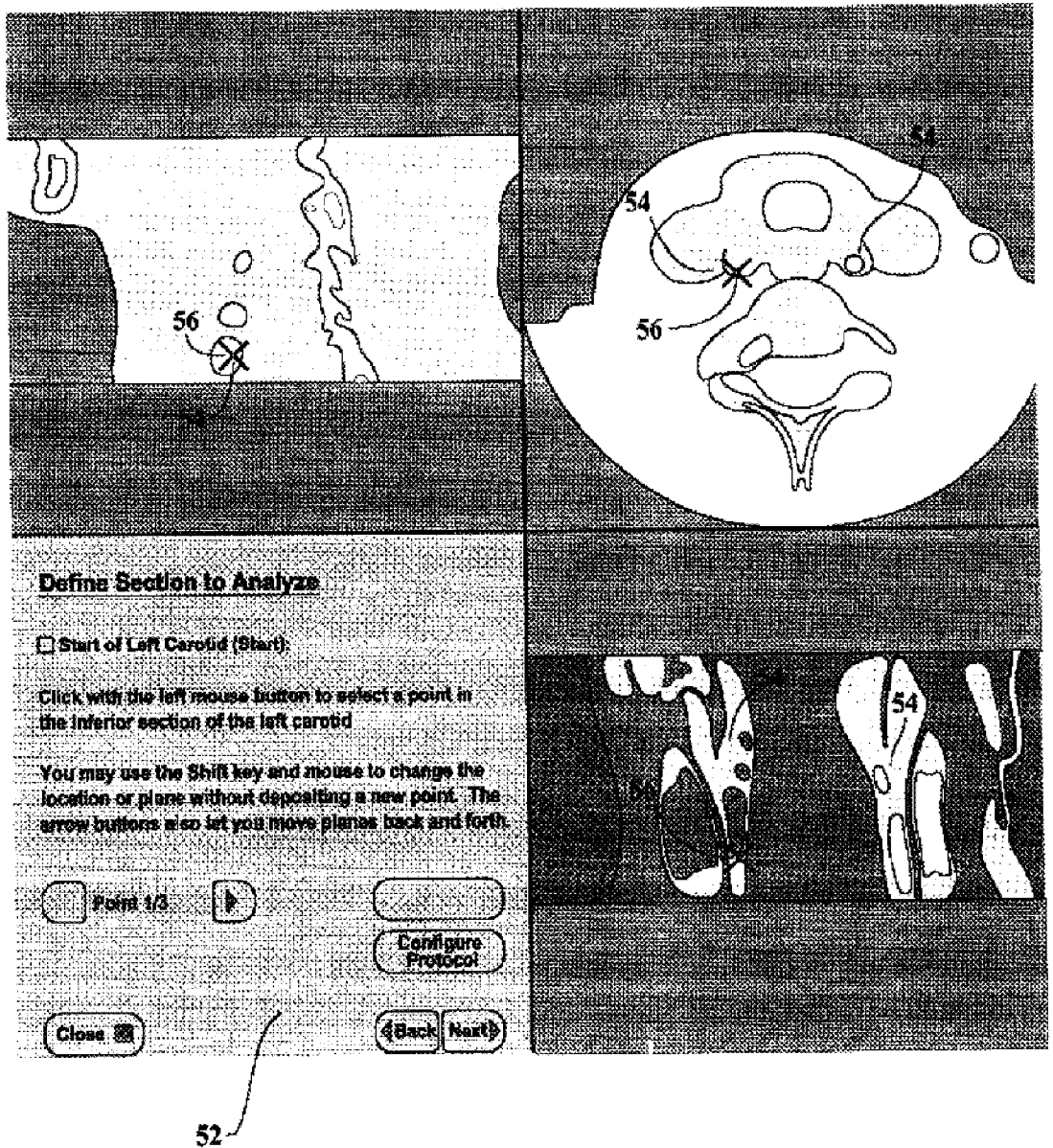
FIG. 3 is a drawing of a computer display of one embodiment of the present invention for the selection of vascular sections to be analyzed.
Figure 4:
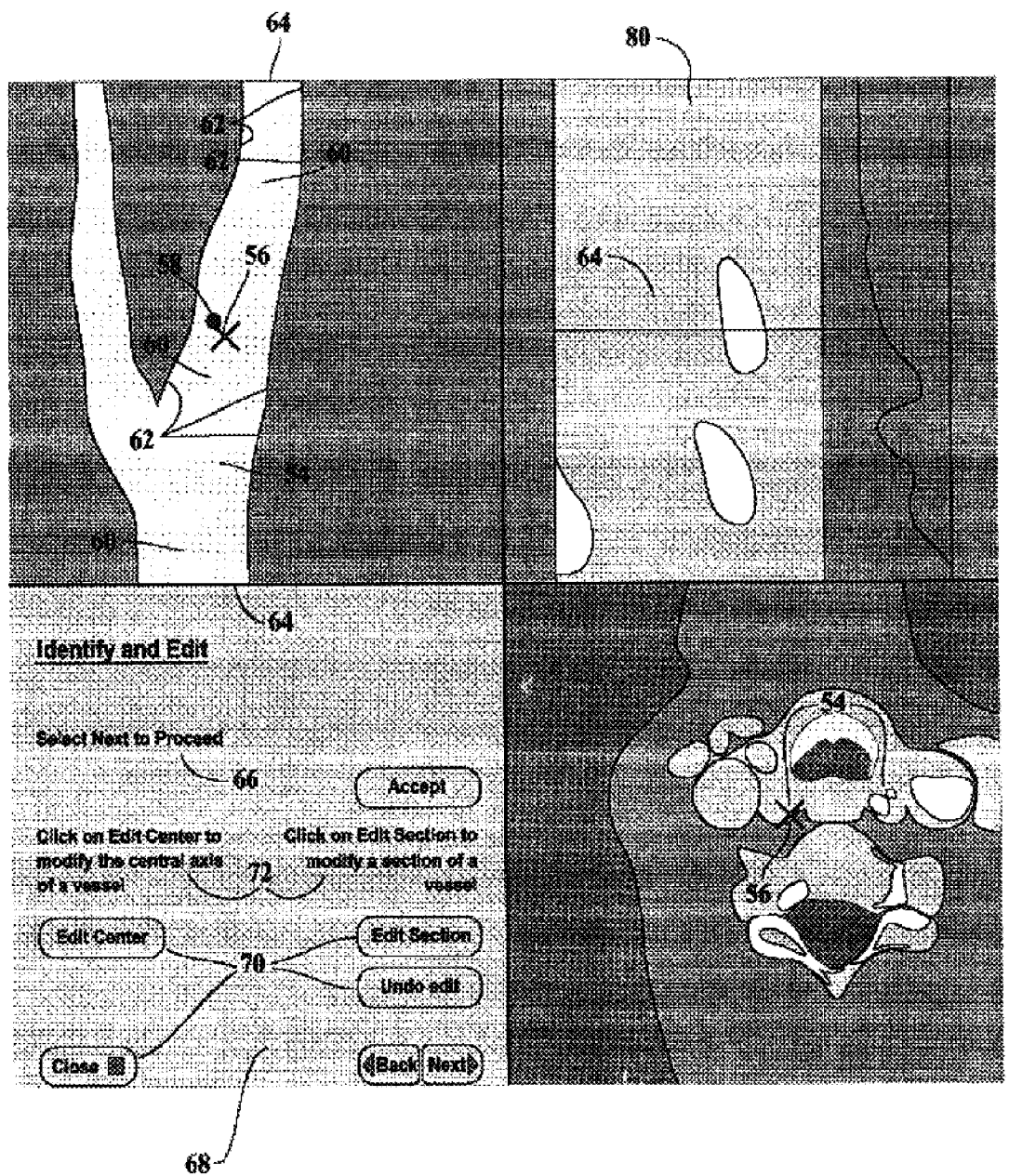
FIG. 4 is a drawing of a computer display showing automated computation of a centerline for vascular sections of interest.

Computer 36, console 40, and display 42 are used in the following steps, in conjunction with a pointing device. The pointing device is, for example, a control on console 40 or a separate device such as a mouse (not shown). In one embodiment and referring to FIG. 3, software executed by computer 36 displays a wizard panel 52 that prompts a user to select locations in a tube-shaped tree, for example, a vascular tree 54, and the user is directed to point 56 to a section of tree 54. This section or region of interest may span across several branches, but the section should be connected. The user then clicks to select either a reformatted slice or a 3D view. Referring to FIG. 4, the software program then locates a center point 58 that is closest to a location 56 pointed to by the user. To compute the center point, a local axis 60 of a selected vessel is computed. In a plane perpendicular to axis 60, the software computes an "average" (i.e., a geometric center) of contour points 62 found around selected point 56. (Contour points 62 are boundary points of vessels 64 or other structures found by computer 36 using contrasts, thresholding, or any other suitable method.) The software then prompts 66 the user for the next point of interest. This process is repeated until the locations of a set of points 56 defined by a given type of anatomy have been indicated by the user. In one embodiment, although the software is programmed with a number of points 56 to be selected for various given types of anatomy, the software provides the user with the option to skip points 56 not relevant for his or her specific needs. In this manner, the user selects a series of points of interest along a centerline of branches that have been identified. Wizard panel 52, in one embodiment, also provides tools (not shown in FIG. 4) to customize the number and/or names of the sections to be designated to permit the software to be tailored to site preferences or anatomical situations.

Figure 6:
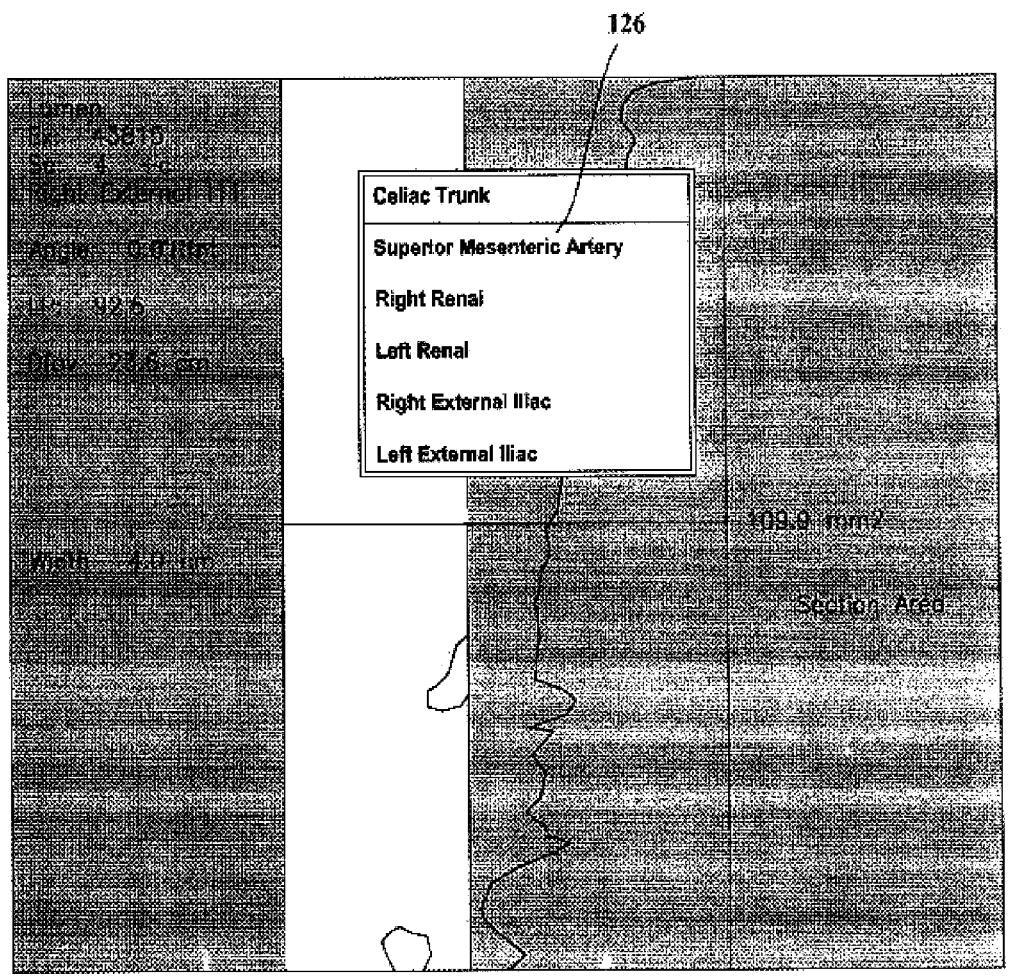
FIG. 6 is a drawing of a computer display showing a branch selection menu.

Next, the software computes a centerline 60 for the vascular sections of interest from the set of points 56 defined during the previous step. A dynamic programming algorithm is used to compute an initial path (not shown) that minimizes a cost function, for example, one that avoids low gray-level values of the image. Next, the software determines planes perpendicular to this path, and on each plane, the software uses an average (i.e., geometric center) of contour points 62 to compute a new center point 58. Vessels 64 are unfolded 80 along centerline 60 defined by new center points 58, and along each branch, the software computes the section area and maximum and minimum diameters for the section. After computation, the software permits the user to edit centerline 60 and the section area for each branch if the results are not deemed correct. A wizard panel 68 provides tools 70 and guidance 72 to perform these actions. Also, one or more views 120, 122, 124 are displayed. Referring to FIG. 6, a menu 126 is available to assist the user in selecting any branch 76, 78 of vascular tree 54 of interest.

In one embodiment, the view or views 120, 122 and 124 displayed is/are a curved view, as a function of the selected branch, reformatted views or 3D views generated as a function of the centerline that has been identified and a location along the centerline, and a selected branch (if there is more than one branch); or a reformatted views or 3D views generated as a function of the identified centerline, a location along the centerline and a selected geometric property of the cross-section boundary of the tube-shaped tree at selected location, as well as the selected branch (if there is more than one).

Also in one embodiment of the present invention, the view or views displayed is/are segmented 3D views, where the section of interest has been identified and a remainder of the patient's anatomy is not visible or attenuated; curved views, as a function of selected branch (if there is more than one); reformatted views or 3D views generated as a function of the centerline that has been identified and a location along the centerline, as well as the selected branch (if there is more than one); reformatted views or 3D views generated as a function of the identified centerline, a location along the centerline and a selected geometric property of the cross-section boundary of the tube-shaped tree at selected location, as well as the selected branch (if there is more than one).

A user is also able to rotate the view around the unfolded selected branch 80 and, by moving the cursor mouse 82, obtain a cross section of a vessel at the cursor position on another view.

Figure 7:
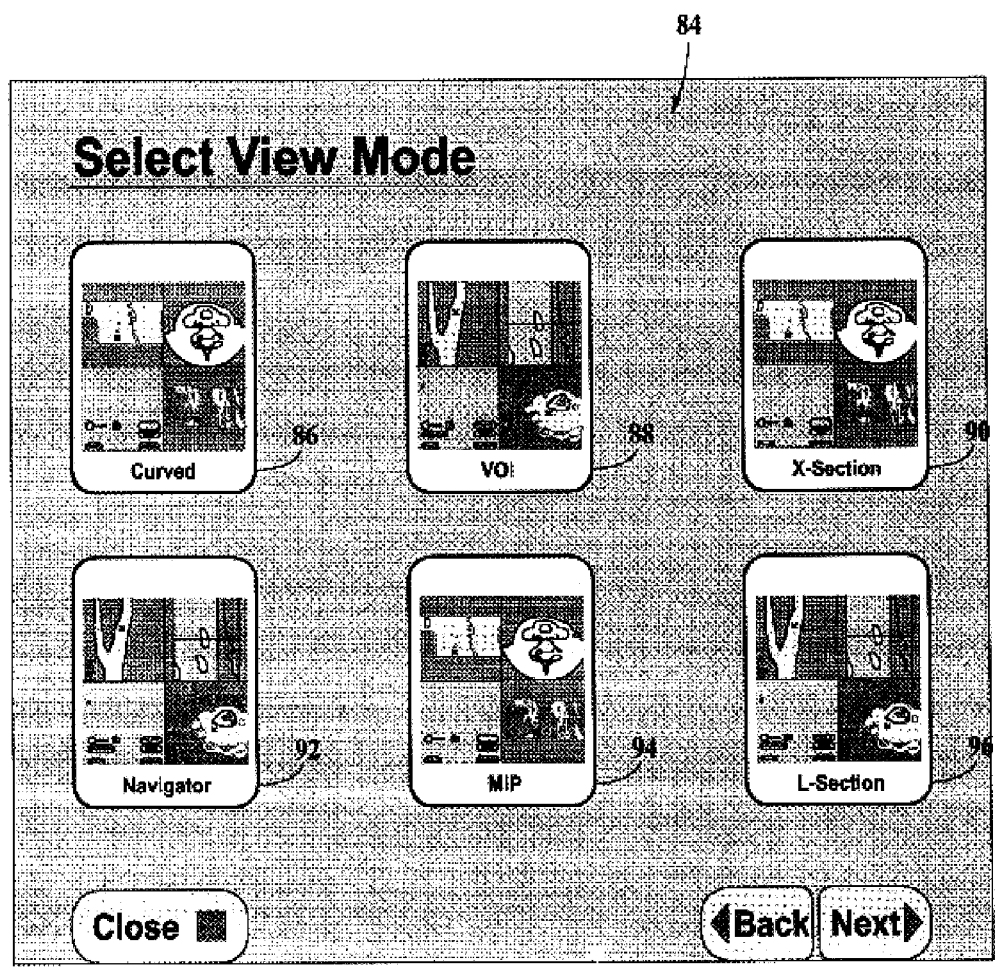
FIG. 7 is a drawing of a computer display showing a palette of advanced display tools.

In one embodiment and referring to FIG. 7, the software next provides a palette 84 of advanced display tools 86, 88, 90, 92, 94, and 96. In one embodiment, these include tools for curved views, with rotation controls; 3D views with automatic segmentation of the region of interest; endovascular 3D views; and automatic adjustment of reformatted slices to display cross-sections, longitudinal sections or specific views to capture the local smallest or largest vascular section.

Figure 5:
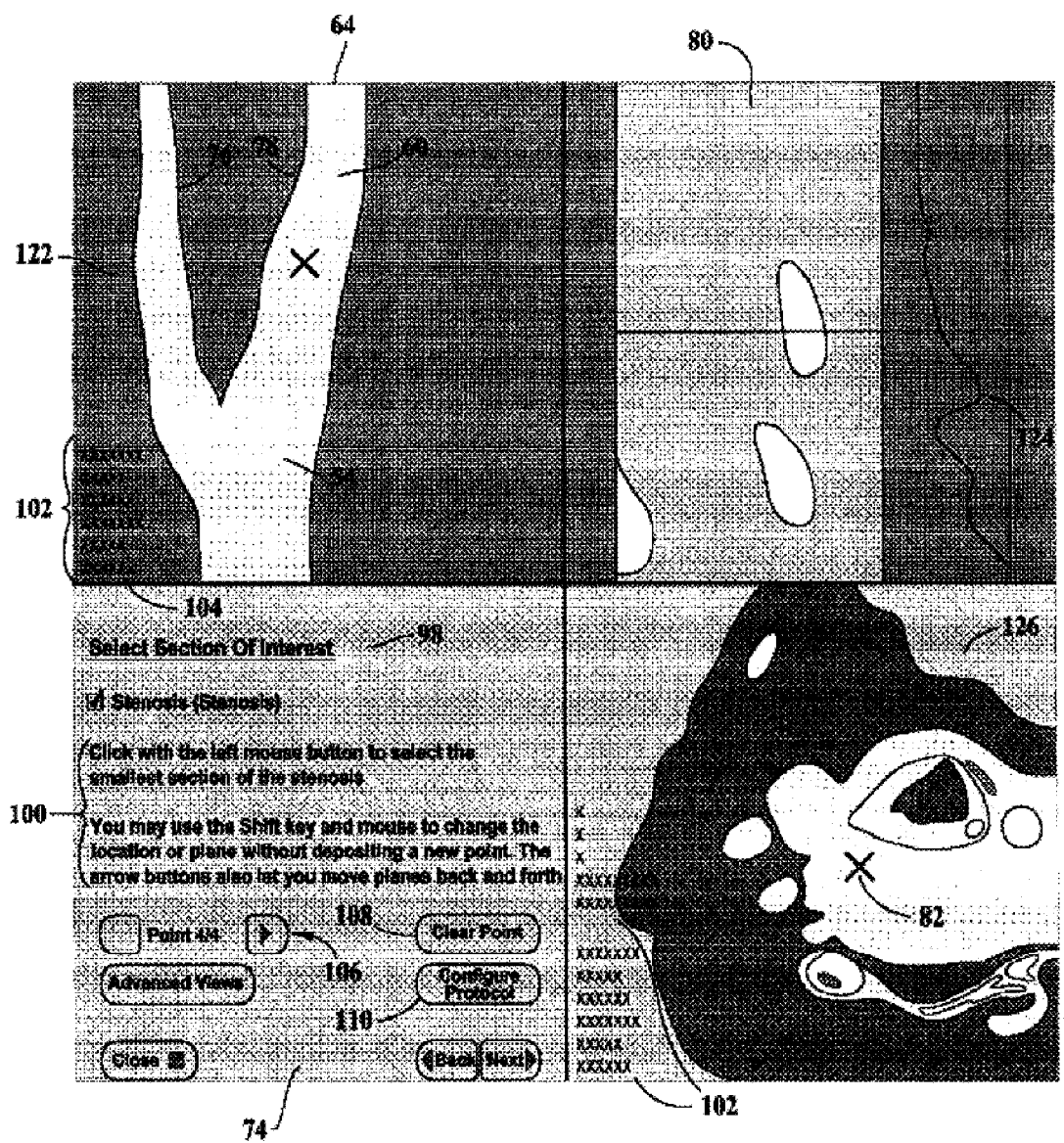
FIG. 5 is a drawing of a computer display for the selection of sections of interest for measurements and reports.

Referring again to FIG. 5, the software prompts 98 the user to designate sections of interest for measurements and reports, for example, certain points where measurements are to be performed or where specific images are to be produced. In one embodiment, the software provides explicit directions 100 and predefined labels 102. Examples of such points of interests include a beginning and an ending of a stenosis or aneurysm section, specific locations that pertain to the placement of endo-vascular prostheses or reference-healthy-sections. Some of these points can be placed by the user, while others can be located automatically. One or more measurements 104 are attached to these points in order to compute section area or diameters, length, tortuosity or volume of a part of a vessel 64. Wizard panel 74 also provides tools 106, 108, 110 to customize the this set of points as well as the measurements that should be performed. Measurements that are automatically made by the software are: automatic measurements of: 3D lengths along the centerline between two locations; computation of a volume of the vascular section between two of these locations; determination of a local cross-section area, maximum and minimum diameter, and/or average diameter at a selected point. These measurements are derived from the identification of the centerline and the contours.

Figure 8:
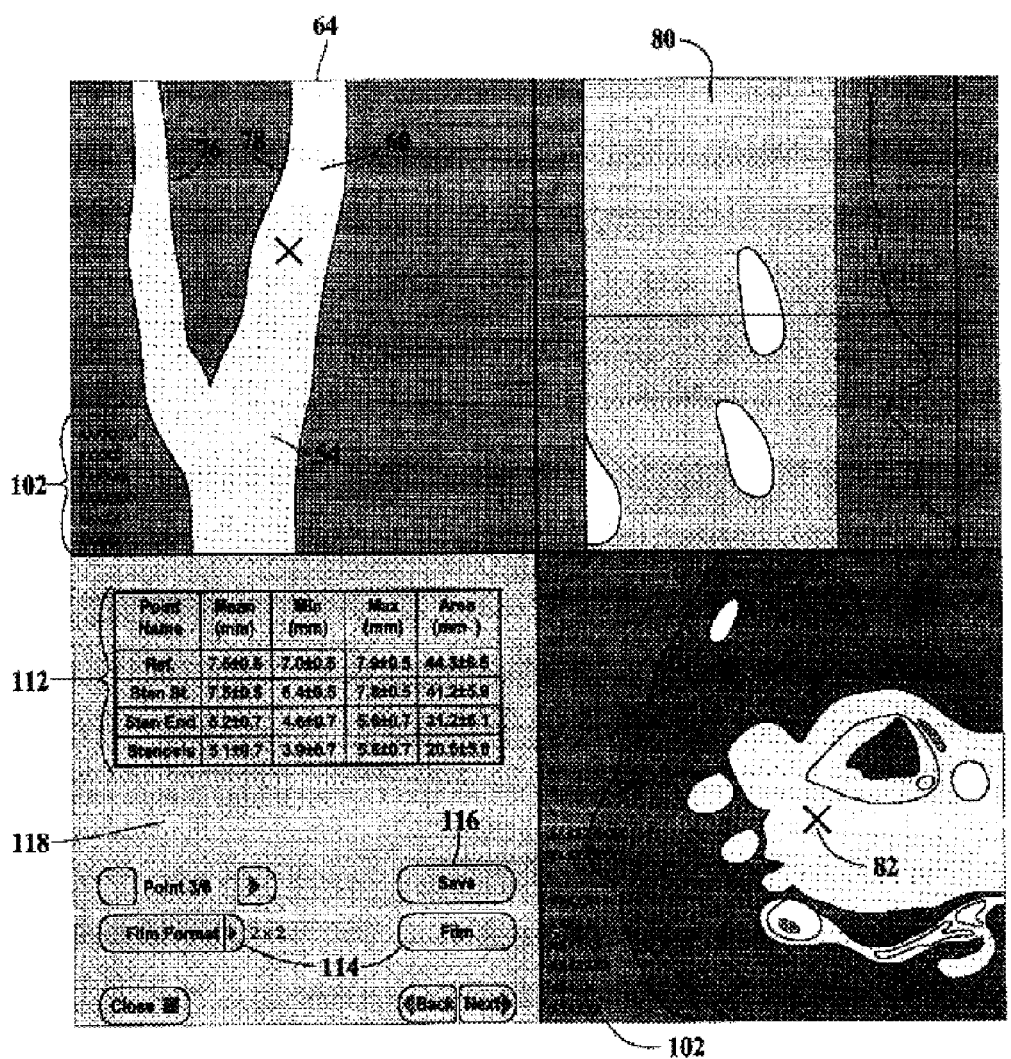
FIG. 8 is another drawing of a computer display for the selection of sections of interest for measurements and reports of one embodiment of the present invention, also showing a table of measurements.
Figure 9:
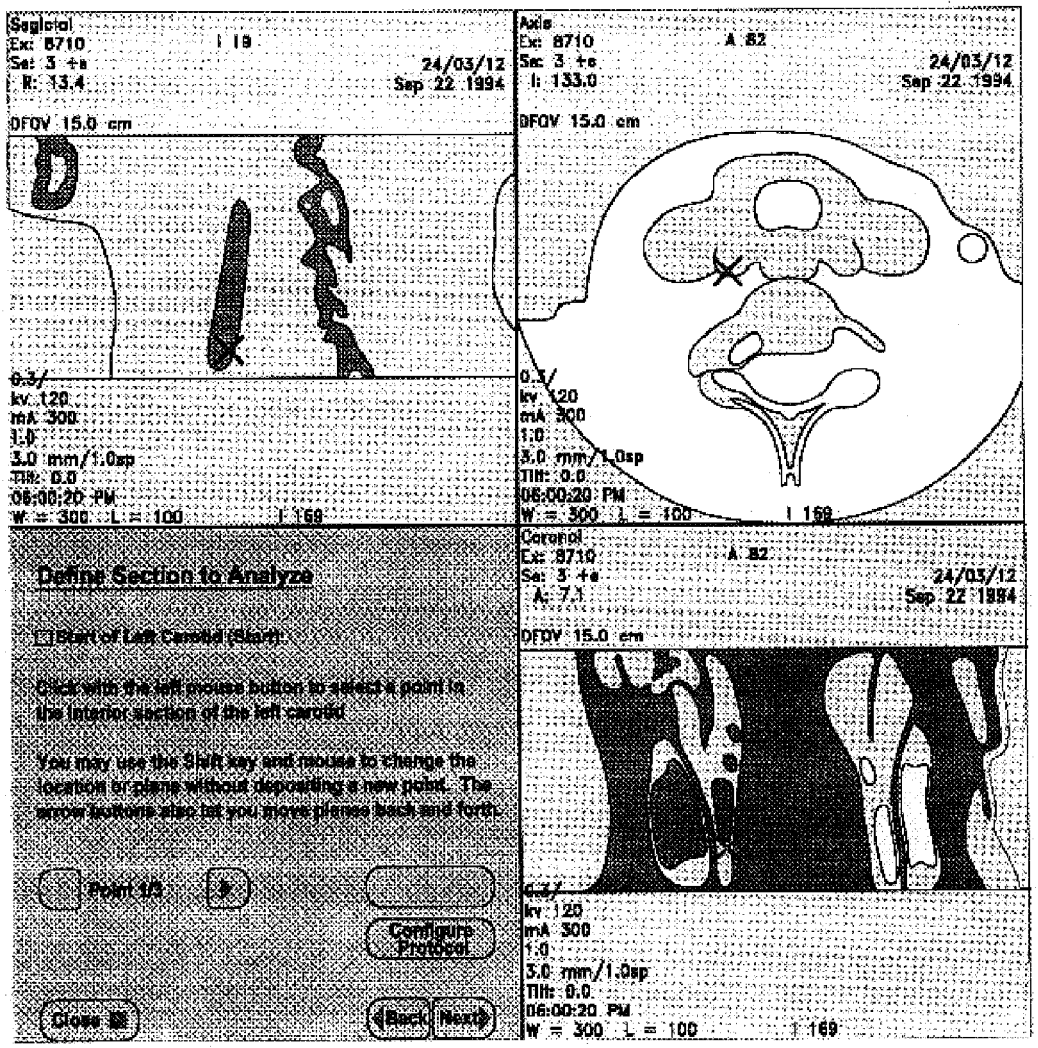
FIGS. 9, 10, 11, and 12 are provided for the convenience of the reader, to more clearly show details of the corresponding positive images that may be obscured in reproductions of the figures.
Figure 10:
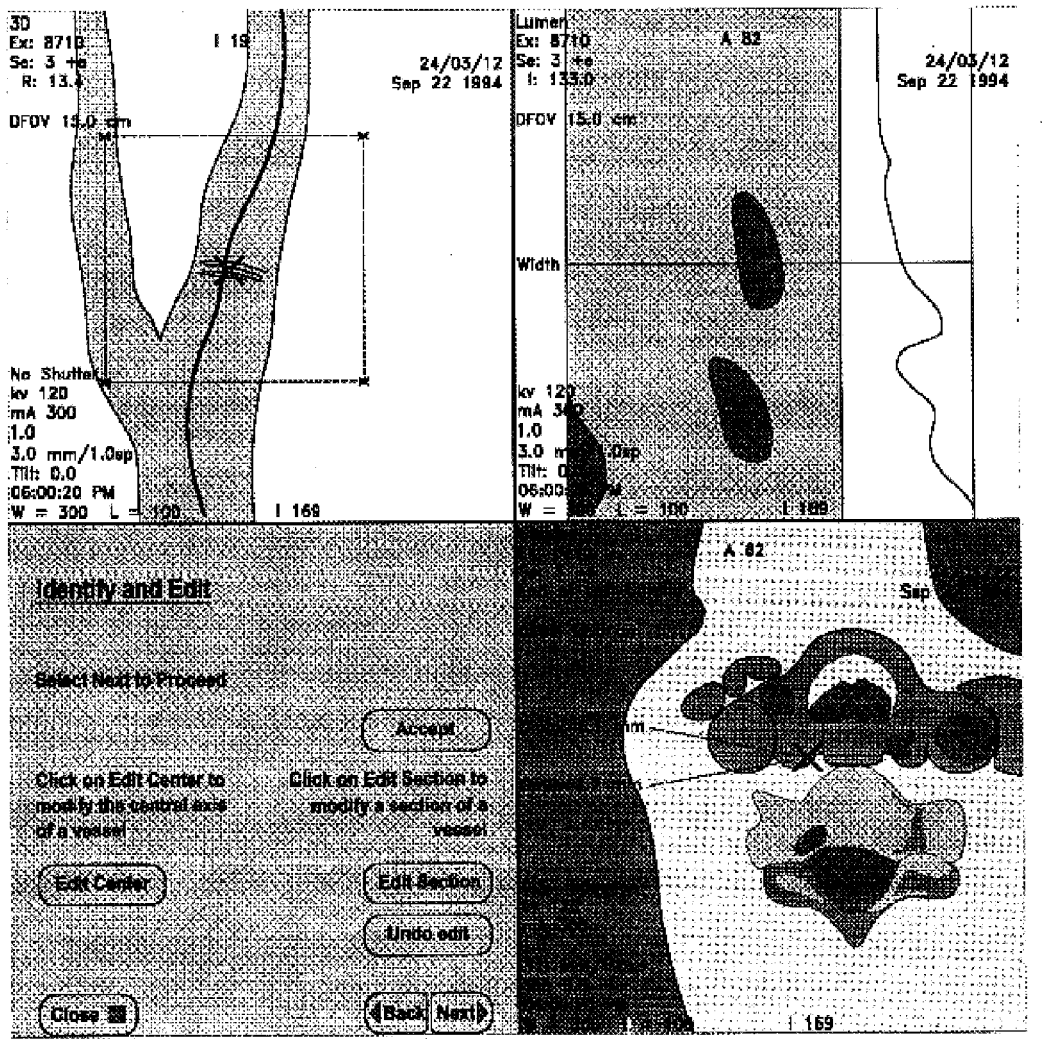
Figure 11:
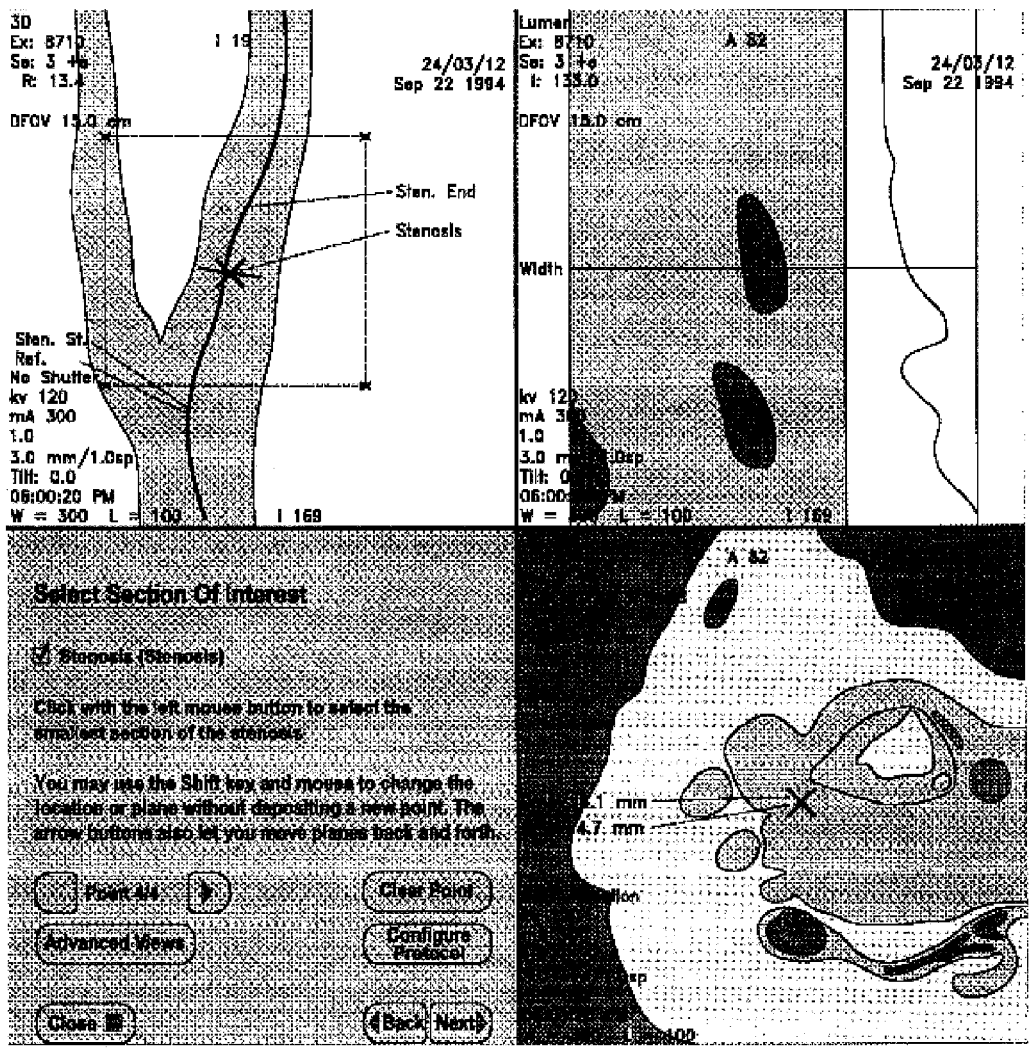
Figure 12:
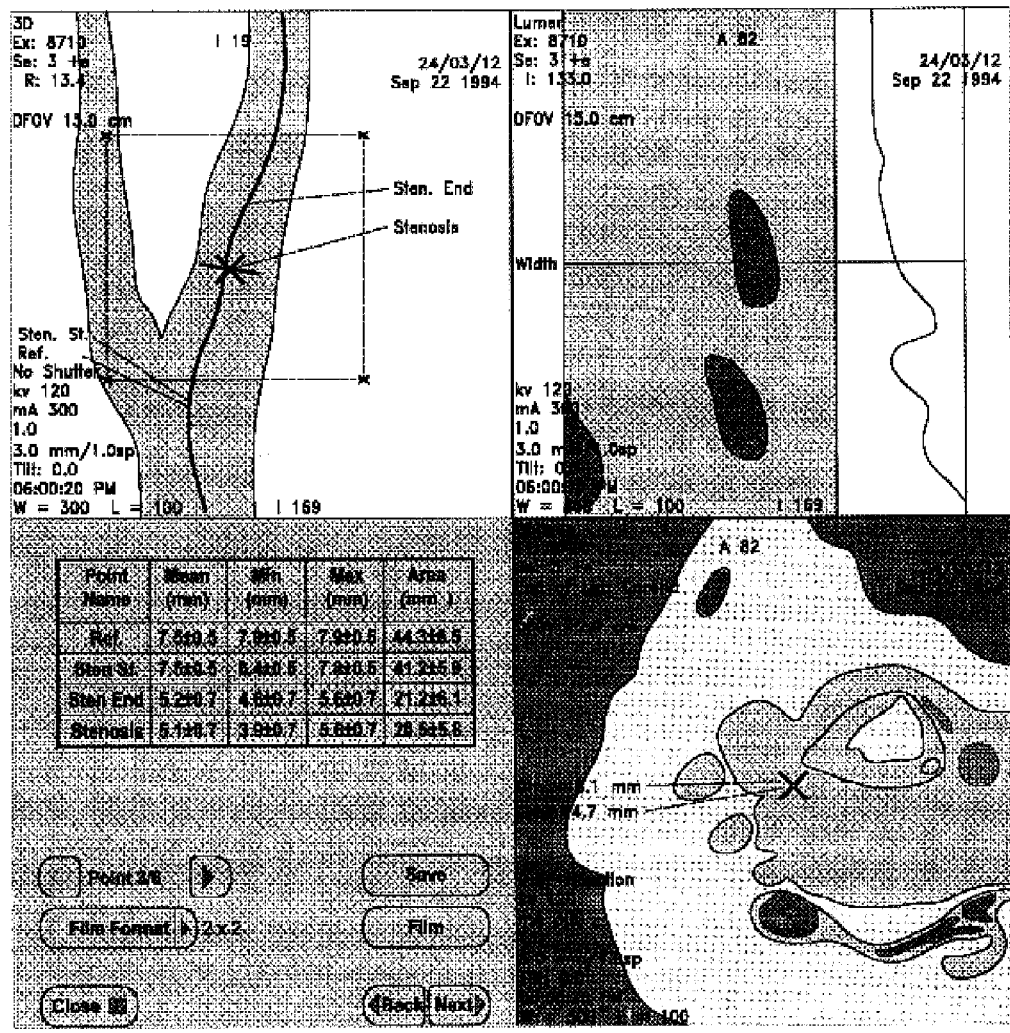

In one embodiment and referring to FIG. 8, result tables 112 are provided to summarize measurements. In one embodiment, printing 114 and storing 116 capability is provided so that a user can either save or print the result tables with a set of significant vessel 64 images. Saving of measurements and selected images can be to a short- or long-term storage medium (including radiological film or paper hard copy) associated with computer 36. The software also provides a wizard panel 118 with tools and guidance to perform these actions. The user can select images to add to the report, if desired.

Embodiments of the present invention provide an analysis methods and apparatus that are fully assisted and usable even with limited training, thereby reducing training costs and is accessible to a larger number of medical users. In addition, automatic results are provided that are more reliable than results found manually. Methods and apparatus of the present invention also significantly increase productivity: aside from automatic tracing, anatomical names are automatically provided, reducing the amount of typing needed. Also, report production is automated. A complete case may be processed in less than 10 minutes versus over an hour with previous methods. Embodiments of the present invention are capable of analyzing several branches of a vascular tree in a single step. Moreover, consistent reports are provided because the format of the report is defined by the software. This consistency is important for referring physicians, because they are able to read them faster and with more confidence, leaving physicians with fewer questions to ask radiologists. Furthermore, embodiments of the present invention save time, produce more complete reports, and provide better image quality than known scanners.

To provide further flexibility, in one embodiment of the present invention, users are given the capability to modify the nature and content of the predefined messages, for example, prompt 98.

Embodiments of the present invention are applicable to selection and analysis of many types of tubular structures, including vascular structures, coronary vessels, and airways. In addition, although embodiments of the present invention have been described in conjunction with a CT imaging systems 10, it will be understood that the present invention is also applicable to other types of imaging systems and images obtained from such systems, as well. Examples of such other types of imaging systems used in other embodiments of the present invention include MR imaging systems and 3-D x-ray imaging systems. In addition, some embodiments of the present invention utilize data computers and displays that are not themselves part of any imaging system. In these cases, the computers obtain data from one or more separate imaging systems, such as via tape, disk, or other storage media, or via a network. At least one such embodiment is configured to accept, handle, and process data from more than one type of imaging system.

While the invention has been described in terms of various specific embodiments, those skilled in the art will recognize that the invention can be practiced with modification within the spirit and scope of the claims.

What is claimed is:

1. A method for analyzing tubular structures in a patient, comprising the steps of:
    displaying a tube-shaped tree representative of a tubular structure in a patient;
    prompting a user to select, from the displayed tube-shaped tree, a region of interest and a location within the region of interest;
    identifying a centerpoint of a structure closest to the selected location within the tube-shaped tree within the region of interest; and
    displaying at least one view of the region of interest selected from the group of views consisting of: a segmented 3-D view having the region of interest identified, a curved view of the selected branch, a reformatted view dependent upon the identified centerpoint, and a 3-D view dependent upon the identified centerpoint.

2. A method in accordance with claim 1 wherein one of the displayed views is selected from the group consisting of a reformatted view dependent upon the identified centerline centerpoint, and a 3-D view dependent upon the identified centerpoint, and wherein the one of the displayed views further includes the selected branch.

3. A method in accordance with claim 1 wherein one of the displayed views is selected from the group consisting of a reformatted view dependent upon the identified centerpoint, and a 3-D view dependent upon the identified centerpoint, and wherein the one of the displayed views includes a location along centerline a centerline and a geometric property of the cross-sectional boundary of the tube-shaped tree at the region of interest.

4. A method in accordance with claim 1 further comprising the steps of:
    identifying branches of the tube-shaped structure;
    prompting a user to select points of interest along a centerline of the branches of the tube-shaped structure; and
    measuring and displaying at least one member of the group consisting of: 3-D lengths along a centerline between two selected points of interest; a volume of the vascular section between two of the selected locations; a cross-sectional area; and a minimum diameter, a maximum diameter, and an average diameter at the selected points of interest.

5. A method in accordance with claim 4 further comprising the step of displaying a pre-defined message guiding said selection of points of interest.

6. A method in accordance with claim 5 wherein the pre-defined messages are selectable by a user.

7. A method in accordance with claim 4 further comprising the step of saving values of measurements a selected displayed views to a storage medium.

8. A method in accordance with claim 7 further comprising the step of display a pre-defined message guiding a selection of measurements and displays to be stored.

9. A method in accordance with claim 8 wherein the pre-defined messages are selectable by a user.

10. A method in accordance with claim 1 further comprising the step of displaying pre-defined messages guiding said selection of the region of interest and the location within the region of interest.

11. A method in accordance with claim 10 wherein the predefined messages are selectable by a user.

12. A method in accordance with claim 1 wherein the displayed tube shaped tree is representative of vascular structures of the patient.

13. A method in accordance with claim 1 wherein the displayed tube shaped tree is representative of coronary structures of the patient.

14. A method in accordance with claim 1 wherein the tube shaped tree is representative of airways of the patient.

15. A device for facilitating the analysis of tubular structures in a patient, said device configured to:

display a tube-shaped tree representative of a tubular structure in a patient;

prompt a user to input a selection of a region of interest and a location within the region of interest from a displayed tube-shaped tree representative of a tubular structure in a patient;

identify a centerpoint of a structure closest to the selected location within a tube-shaped tree within a selected region of interest; and display at least one view of the region of interest selected from the group of views consisting of: a segmented 3-D view having the region of interest identified, a curved view of the selected branch, a reformatted view dependent upon the identified centerpoint, and a 3-D view dependent upon the identified centerpoint.

16. A device in accordance with claim 15 wherein one of the displayed views is selected from the group consisting of a reformatted view dependent upon the identified centerpoint, and a 3-D view dependent upon the identified centerpoint, and wherein the one of the displayed views further includes the selected branch.

17. A device in accordance with claim 15 wherein one of the displayed views is selected from the group consisting of a reformatted view dependent upon the identified centerpoint, and a 3-D view dependent upon the identified centerpoint, and wherein the one of the displayed views includes a location along a centerline and a geometric property of the cross-sectional boundary of the tube-shaped tree at the region of interest.

18. A device in accordance with claim 15 further configured to:

input a selection of branches of the tube-shaped structure;

prompt a user to input a selection of points of interest along a centerline of the branches of the tube-shaped structure; and measure and display at least one member of the group consisting of: 3-D lengths along a centerline between two selected points of interest; a volume of the vascular section between two of the selected locations; a cross-sectional area; and a minimum diameter, a maximum diameter, and an average diameter at the selected points of interest.

19. A device in accordance with claim 18 further configured to display a pre-defined message guiding said selection of points of interest.

20. A device in accordance with claim 19 wherein the pre-defined messages are selectable by a user.

21. A device in accordance with claim 18 further configured to save values of measurements a selected displayed views to a storage medium.

22. A device in accordance with claim 21 further configured to display a pre-defined message guiding a selection of measurements and displays to be stored.

23. A device in accordance with claim 22 wherein the pre-defined messages are selectable by a user.

24. A device in accordance with claim 15 further configured to display pre-defined messages guiding said selection of the region of interest and the location within the region of interest.

25. A device in accordance with claim 24 wherein the predefined messages are selectable by a user.

26. A device in accordance with claim 15 configured to display a tube shaped tree representative of vascular structures of the patient.

27. A device in accordance with claim 15 configured to display a tube shaped tree representative of coronary structures of the patient.

28. A device in accordance with claim 15 configured to display a tube shaped tree representative of airways of the patient.

* * * * *